United States Patent
Richards et al.

(10) Patent No.: US 10,702,323 B2
(45) Date of Patent: Jul. 7, 2020

(54) SPINAL FIXATION ROD BENDING INSTRUMENT

(71) Applicant: Aesculap AG, Tuttlingen (DE)

(72) Inventors: Robert Leslie Richards, Minneapolis, MN (US); Ernest Corrao, Bethel, CT (US)

(73) Assignee: Aesculap AG (DE)

( * ) Notice: Subject to any disclaimer, the term of this patent is extended or adjusted under 35 U.S.C. 154(b) by 131 days.

(21) Appl. No.: 15/939,512

(22) Filed: Mar. 29, 2018

(65) Prior Publication Data
US 2019/0298428 A1 Oct. 3, 2019

(51) Int. Cl.
*A61B 17/88* (2006.01)
*A61B 17/70* (2006.01)
*B21D 7/06* (2006.01)

(52) U.S. Cl.
CPC ...... *A61B 17/8863* (2013.01); *A61B 17/7002* (2013.01); *A61B 17/7011* (2013.01); *A61B 17/7074* (2013.01); *B21D 7/063* (2013.01)

(58) Field of Classification Search
CPC ............ A61B 17/7074; A61B 17/8863; A61B 17/7002; A61B 17/7011; B21D 7/063
See application file for complete search history.

(56) References Cited

U.S. PATENT DOCUMENTS

| 4,474,046 | A | 10/1984 | Cook |
| 5,390,522 | A * | 2/1995 | Dircks ............... B21D 7/024 72/217 |
| 5,490,409 | A | 2/1996 | Weber |
| 5,761,950 | A * | 6/1998 | Chiu .................. B21D 7/063 72/389.1 |
| 6,006,581 | A | 12/1999 | Holmes |
| 6,931,908 | B1 * | 8/2005 | Mitson ................ B21D 7/04 72/213 |
| 7,454,939 | B2 | 11/2008 | Garner et al. |
| 9,044,285 | B2 | 6/2015 | Harper |
| 9,162,273 | B1 * | 10/2015 | Chiu .................... B21D 7/06 |
| 9,433,988 | B1 * | 9/2016 | Huang ............... B21D 7/066 |
| 9,642,664 | B2 | 5/2017 | Ryan et al. |
| 10,189,069 | B1 * | 1/2019 | Huang ............... B21D 7/022 |
| 2009/0222020 | A1 * | 9/2009 | Schmuck .......... A61B 17/8863 606/101 |
| 2012/0240655 | A1 * | 9/2012 | Houle ................ B21D 7/063 72/476 |
| 2014/0364860 | A1 * | 12/2014 | Knoepfle ......... A61B 17/8863 606/101 |
| 2016/0346026 | A1 * | 12/2016 | Bootwala ......... A61B 17/8863 |
| 2017/0042597 | A1 * | 2/2017 | Rinner ............. A61B 17/8863 |

* cited by examiner

*Primary Examiner* — Tessa M Matthews
(74) *Attorney, Agent, or Firm* — RatnerPrestia (57) ABSTRACT

An instrument for bending a surgical implant about a bending axis includes a handle defining a receiving area for receiving the surgical implant. A lever is pivotably connected to the handle about a pivot axis that can be orthogonal to the bending axis. A movable linkage can be connected to the lever for movement with the lever. The moveable linkage can be configured to bend the surgical implant about the bending axis upon pivoting the lever about the pivot axis.

13 Claims, 8 Drawing Sheets

FIG. 10B ated to each other. Many spinal fixation systems employ a spinal fixation rod for supporting the spine and for properly positioning components of the spine for various treatment purposes. The spinal rod, which is generally formed of a metal, such as stainless steel or titanium, may be implanted to correct deformities, prevent movement of vertebral bodies relative to each other or for other purposes. Vertebral anchors, comprising pins, bolts, screws, and hooks, engage the vertebrae and connect the rod to different vertebrae.

SPINAL FIXATION ROD BENDING INSTRUMENT

FIELD

The field of the invention relates generally to an instrument for bending a spinal fixation rod.

BACKGROUND

As is disclosed in U.S. Pat. No. 7,454,939, which is incorporated by reference herein, spinal fixation systems may be used in surgery to align, adjust and/or fix portions of the spinal column, i.e., vertebrae, in a desired spatial relationship relative to each other. Many spinal fixation systems employ a spinal fixation rod for supporting the spine and for properly positioning components of the spine for various treatment purposes. The spinal rod, which is generally formed of a metal, such as stainless steel or titanium, may be implanted to correct deformities, prevent movement of vertebral bodies relative to each other or for other purposes. Vertebral anchors, comprising pins, bolts, screws, and hooks, engage the vertebrae and connect the rod to different vertebrae.

Spinal fixation rods are frequently oriented at various angles and positions due to the anatomical structure of the patient, the physiological problem being treated, and the preference of the physician. The size, length and bend of each spinal rod depend on the size, number and position of the vertebrae to be held in a desired spatial relationship relative to each other, which is generally different for each patient. A rod may be bent, as desired, to conform to a desired curvature of the spinal column in one or more of the anatomic planes, in order to fit the rod into the vertebral anchors.

In the current state of the art, bending of spinal rods is typically accomplished using a hand-operated instrument, commonly known as a "French bender." The French bender is a pliers-like instrument. Because spinal rods are formed of materials that are not easily bendable, such as titanium, a significant amount of force is required to bend the rods. If one hand is used to operate the French bender, then the physician must rotate that hand in an awkward orientation in order to properly view the changing curve of the rod as the handles are squeezed together, and the awkward orientation of the physician's single hand could either prevent the physician from applying the appropriate amount of force required for bending the rod or lead to slippage of the instrument. Accordingly, many physicians use both hands to operate the French bender, which prevents the physician from using a free hand to manipulate the rod in the French bender (or other manual activity).

In view of the foregoing, there exists opportunities for improving upon the structure and operation of a hand-operated instrument for bending a rod, such as a French Bender.

SUMMARY

The drawbacks of conventional rod bending techniques are resolved in many respects with instruments in accordance with the invention.

In one embodiment, an instrument for bending a surgical implant about a bending axis includes a handle defining a receiving area for receiving the surgical implant. A lever is pivotably connected to the handle about a pivot axis that is orthogonal to the bending axis. A movable linkage is connected to the lever for movement therewith. The moveable linkage is configured to bend the surgical implant about the bending axis upon pivoting the lever about the pivot axis.

In another embodiment, an instrument for bending a surgical implant includes a handle defining a receiving area for receiving the surgical implant. A lever is pivotably connected to the handle about a pivot axis. A movable linkage is connected to the lever. The moveable linkage is configured to translate in a first direction to bend the surgical implant about the bending axis upon pivoting the lever about the pivot axis. A friction member extends from the moveable linkage for limiting translation of the moveable linkage in a second direction that is opposite the first direction upon releasing the lever.

In yet another embodiment, an instrument for bending a surgical rod includes a handle defining a receiving area for receiving the surgical rod. A lever is pivotably connected to the handle. A movable linkage is connected to the lever. The moveable linkage is configured to bend the surgical rod upon pivoting the lever. A template rod holder is mounted to one of the handle, the lever and the moveable linkage at a location adjacent the receiving area. The template rod holder is configured for holding a template rod having a bent shape that can be used as a template for bending the surgical rod.

In yet another embodiment, an instrument for bending a surgical implant having an elongated axis includes a handle defining a receiving area for receiving the surgical implant. A lever is pivotably connected to the handle about a pivot axis that is parallel to the elongated axis of the surgical implant.

BRIEF DESCRIPTION OF THE DRAWINGS

The foregoing summary and the following detailed description will be better understood in conjunction with non-limiting examples shown in the drawing figures, of which.

DETAILED DESCRIPTION OF THE PREFERRED EMBODIMENTS

FIGS. 1-6 depict a spinal fixation rod bending instrument 10 (instrument, hereinafter) according to one exemplary embodiment of the invention. Referring generally to the features of the instrument 10, the instrument 10 comprises a handle 12, and a lever 14 that is pivotably mounted to the handle 12 by a pin 16. A pin 17 is mounted to the handle 12 as well as a slot 19 formed in the lever 14 to limit pivoting motion of the lever 14. A pawl 18 is pivotably mounted in a crescent-shaped recess 20 (FIG. 4) formed in the lever 14. A spring arm 22 (FIG. 4) biases the pawl 18 toward the underside of a carriage 24. The carriage 24 is translatably positioned (in a ratcheting fashion) within an elongated opening 26 formed in the handle 12. A central roller 28 is mounted to the top end of the carriage 24. The central roller 28 together with the pawl 18 and carriage 24 form a movable linkage, which is connected (either directly or indirectly) to the lever 14, for bending a rod 130 against two side rollers 30a and 30b that are each attached to the handle 12 by a fastener 36.

Figure 1:
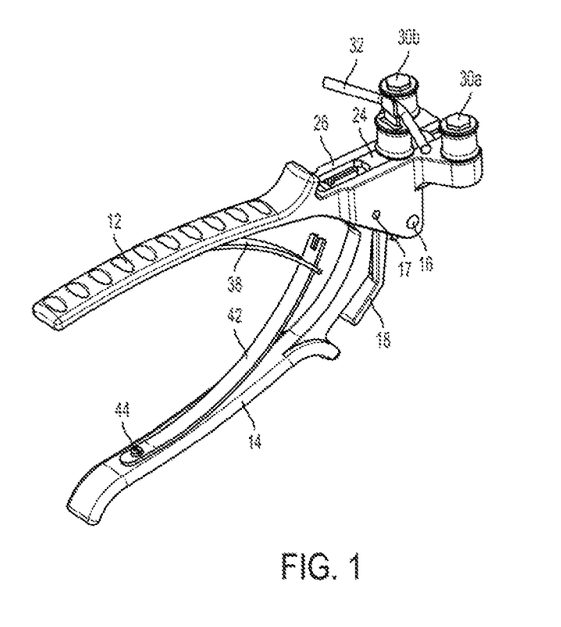
FIG. 1 is an isometric view of a spinal fixation rod bending instrument (instrument, hereinafter) according to one exemplary embodiment of the invention.
Figure 2:
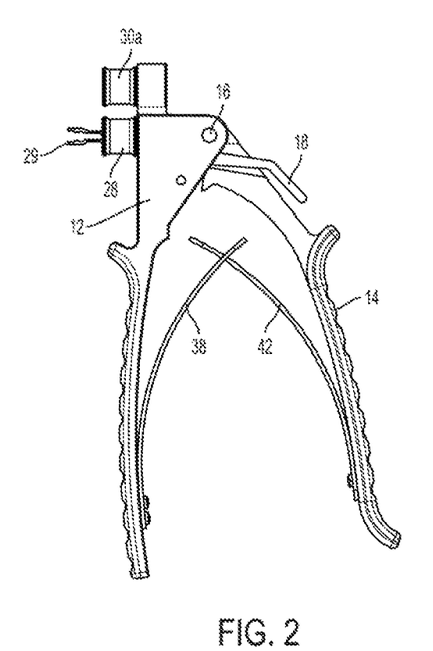
FIG. 2 is a side elevation view of the instrument of FIG. 1.
Figure 3:
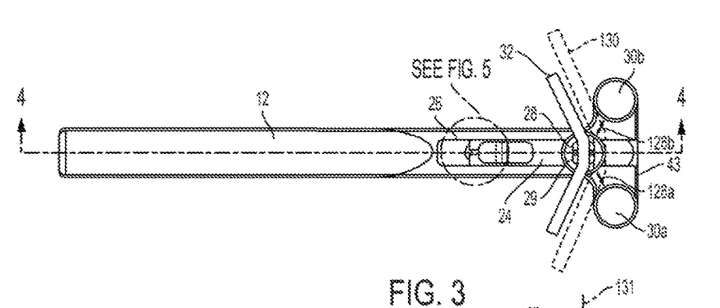
FIG. 3 is a top plan view of the instrument of FIG. 1.
Figure 4:
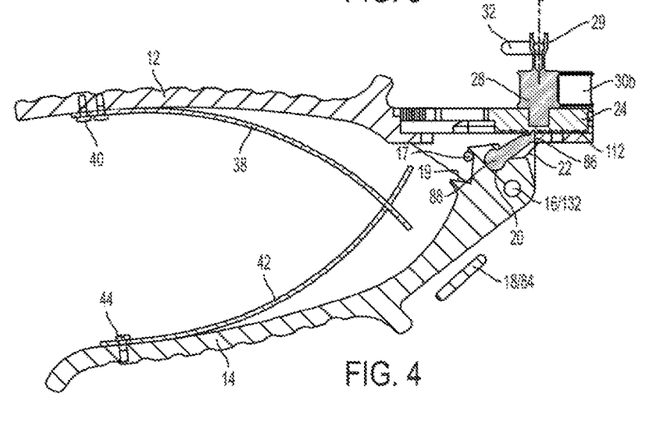
FIG. 4 is a cross-sectional side view of the instrument of FIG. 3 taken along the lines 4-4.

A resilient spring clip 29 having two arms that are spaced apart is mounted to the top side of the central roller 28. The clip 29 is configured for retaining a template rod 32, the purpose of which will be described later. It is noted that the template rod 32 is shown in FIGS. 1, 3 and 4, but is omitted from FIGS. 2 and 6.

A spring 38 in the form of an elongated and curved flat plate is mounted to the handle 12 at its proximal end by one or more fasteners 40. The spring 38 has a prong 37 at its distal end. A second spring 42 is mounted to the lever 14 at its proximal end by one or more fasteners 44. The spring 42 has a slot 39 at its distal end. The prong 37 is positioned within the slot 39, thereby coupling the springs 38 and 42 together. Together, the springs 38 and 42 bias the lever 14 apart from the handle 12.

Reference will now be made to the individual components of the instrument 10.

FIGS. 7A-7D depict the handle 12. The handle 12 is an elongated member extending between a proximal end 41 and a distal end 43. The proximal end 41 includes a handle portion 46 for grasping by a user, whereas the distal end 43 includes a tool head portion for receiving a rod 130 to be bent. The handle portion 46 extends from the proximal end 41 and terminates at an upwardly protruding finger tab 47 that is disposed on the top surface 48. The top surface 48 of the handle portion 46 may be knurled, roughened or ribbed (for example) to enhance grasping by a user.

Two vertically oriented triangular legs 50 are positioned at the distal end 43 of the handle 12. Each leg 50 includes a hole 52 for receiving the pin 17, and another hole 54 for receiving the pin 16. A gap 51 is defined between the legs 50 for accommodating the pivoting distal end of the lever 14. An opening 26 in the form of an elongated slot passes through the top surface of the handle 12 and intersects the gap 51 in the vertical direction.

Two arms 56a and 56b extend horizontally from the distal end 43 of the handle 12 in opposite directions. The arms 56a and 56b are positioned at an elevation above the legs 50. The arm 56a includes a vertically extending hole 57a for receiving the side roller 30a and a fastener 36. Similarly, the arm 56b includes a hole 57b for receiving the side roller 30b and a fastener 36. The side rollers 30a and 30b are positioned at the top side of the arms 56a and 56b, respectively, whereas the fasteners 36 reside on the bottom side of the arms 56a and 56b. The fasteners 36 are threadedly connected to holes formed within the side rollers 30a and 30b.

Figure 7A:
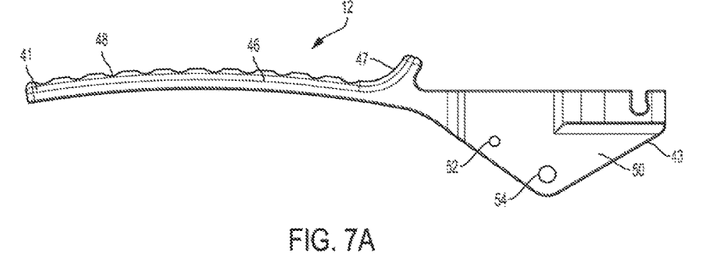
FIG. 7A is a side elevation view of the handle of the instrument of FIG. 1.
Figure 7B:
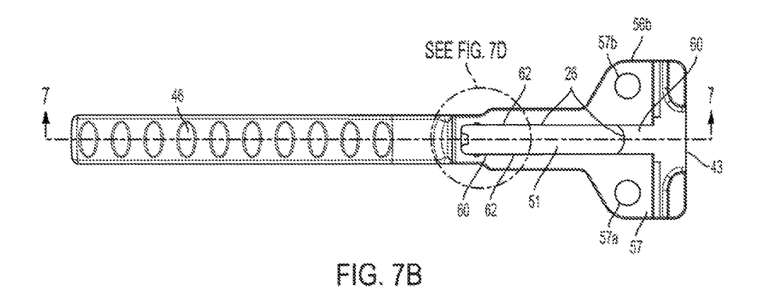
FIG. 7B is a top plan view of the handle of FIG. 7A.
Figure 7C:
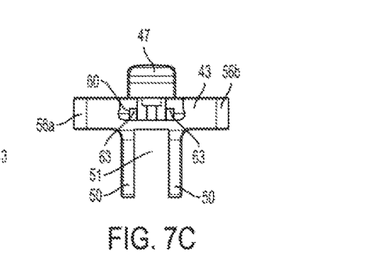
FIG. 7C is a front elevation view of the handle of FIG. 7A.
Figure 7D:
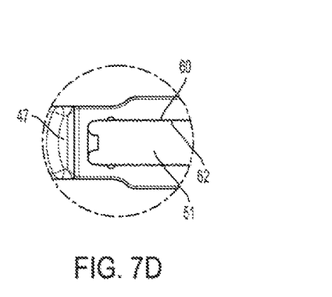
FIG. 7D is a detailed view of one area of FIG. 7B.

A substantially rectangular channel 60 in the form of an elongated slot extends horizontally from the finger tab 47 to the distal end 43. The channel 60 is also defined between the arms 56a and 56b. As best shown in FIG. 7C, a top shoulder 63 is formed on the top side of at least a portion of the channel 60 for constraining the carriage 24 within the channel 60. The channel 60 intersects the slot 26 in the horizontal direction. As best shown in FIG. 7D, at the proximal portion of the channel 60, the opposing horizontally extending sidewalls each includes gear teeth 62. The gear teeth 62 are configured to engage with opposing teeth 64 on the carriage 24. The shape of the individual gear teeth 62 and 64 can vary.

Figures 8A, 8B, 8C:
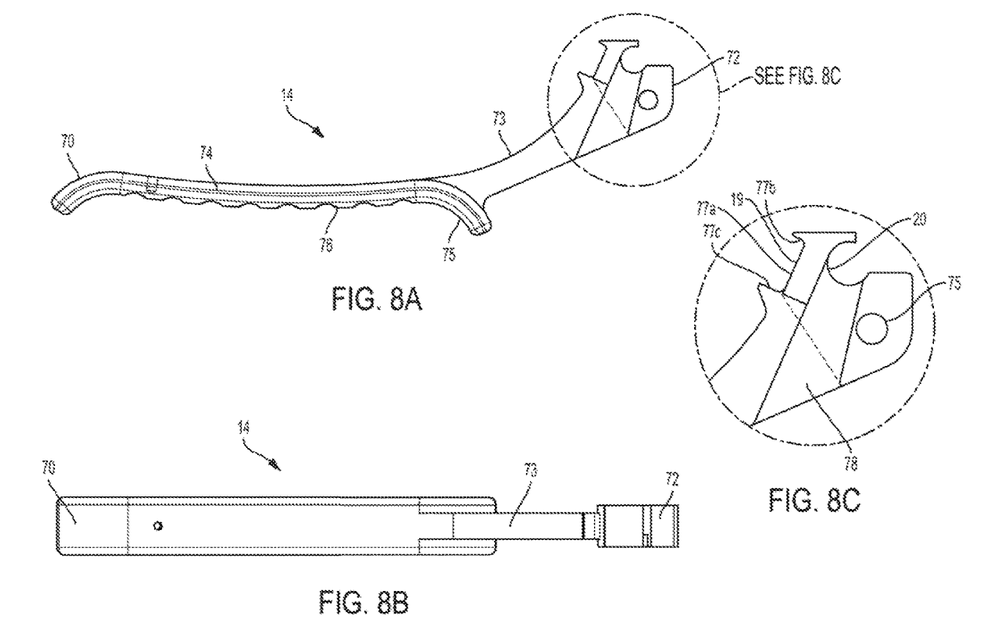
FIG. 8A is a side elevation view of a lever of the instrument of FIG. 1.
FIG. 8B is a top plan view of the lever of FIG. 8A.
FIG. 8C is a detailed view of the lever of FIG. 8A.
Figure 9A:
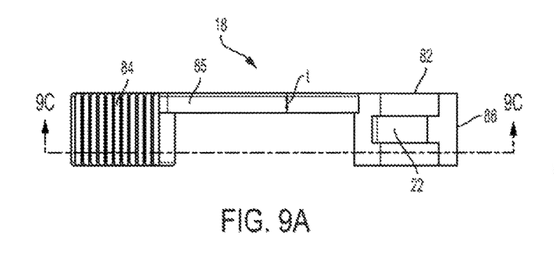
FIG. 9A is a bottom plan view of a pawl of the instrument of FIG. 1.
Figure 9B:
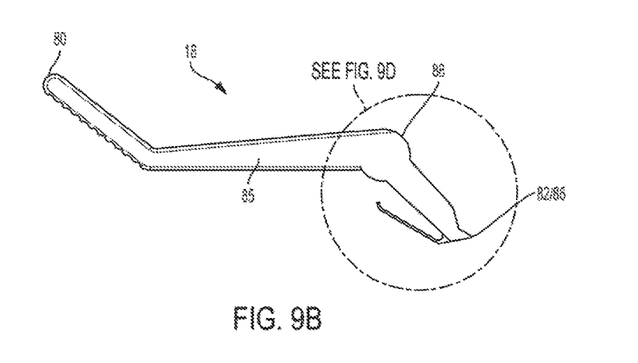
FIG. 9B is a side elevation view of the pawl of FIG. 9A.
Figure 9C:
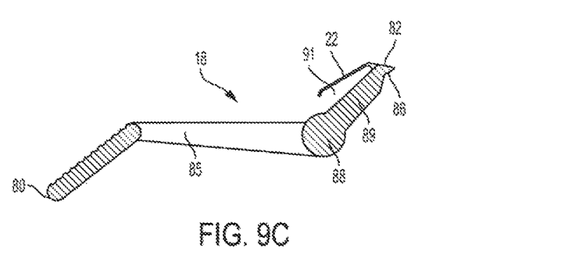
FIG. 9C is a cross-sectional view of the pawl of FIG. 9A taken along the lines 9C-9C.
Figure 9D:
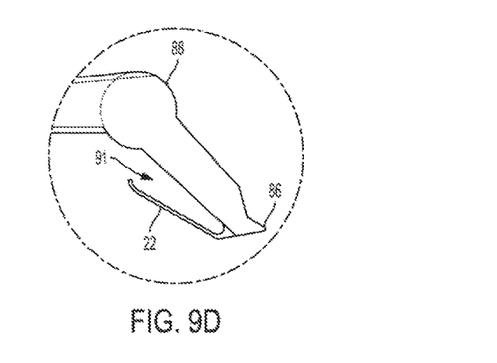
FIG. 9D is a detailed view of the pawl of FIG. 9B.

FIGS. 8A-8C depict the lever 14 of the instrument 10. The lever 14 is an elongated body extending between a proximal end 70 and a distal end 72. The proximal end 70 includes a handle portion 74, whereas the distal end 72 includes a head portion 73. The handle portion 74 extends from the proximal end 70 and terminates at a downwardly protruding rounded finger tab 75 that is disposed on the bottom surface 76. The bottom surface 76 of the handle portion 74 may be knurled, roughened or ribbed (for example) to enhance grasping by a user.

The head portion 73 of the lever 14 extends in a distal direction from the finger tab 75. The head portion 73 includes the crescent-shaped recess 20 at its distal end for accommodating a cylindrical segment of the pawl 18 (see FIG. 4). The head portion 73 also includes a hole 75 for receiving the pin 16. The pivot axis of the head portion 73 of the handle 12 is the longitudinal axis of the hole 75. The slot 19 is formed in the head portion 73 opposite the hole 75. The pin 17 is positioned within the slot 19. The slot 19 is bounded by three walls including a long wall 77a and two opposing walls 77b and 77c, whereby the pin 77a travels along the long wall 77a and the two opposing walls 77b and 77c act as boundaries for travel of the pin 17, thereby limiting pivoting motion of the lever 14. A recessed region 78 (see FIGS. 6 and 8C) in the form of a depression is provided on the side wall of the head portion 73 for accommodating the pawl 18.

FIGS. 9A-9D depict the pawl 18 of the instrument 10. The pawl 18 is an elongated body having a proximal end 80, a distal end 82, and an intermediate section in the form of an arm 85 that extends between the proximal end 80 and the distal end 82. The proximal end 80 extends at an upward angle with respect to the arm 85 and the distal end 82 extends at a downward angle with respect to the arm 85, or vice versa.

The proximal end 80 of the pawl 18 includes a finger tab 84 having a ribbed outer surface for gripping by a user. The thickness 't' of the arm 85 is reduced as compared to the remainder of the body of the pawl 18. In an assembled form of the instrument, the reduced thickness arm 85 resides in the recessed region 78 of the lever 14.

The distal end 82 of the pawl 18 terminates at a right-angle edge comprising a tooth 86. The tooth 86 is configured for interacting with right-angle teeth 112 on the bottom side of the carriage 24 as a ratchet mechanism, as will be described later.

A cylinder 88, which is defined at the intersection of the arm 85 and the distal end 82, is sized to be received in the crescent shaped recess 20 of the lever 14. The cylinder 88 (as well as the remainder of the pawl 18) is rotatable within the recess 20 about the lever 14. A segment 89 extends between the cylinder 88 and the tooth 86. The spring arm 22 is mounted to the segment 89 at a location near the tooth 86. The spring arm 22 extends from the distal end 82 of the pawl 18 such that a gap 91 is formed between the spring arm 22 and the segment 89. The spring arm 22 is configured to flex within the gap 91. The spring arm 22 may be integrated with the pawl 18, or, alternatively, the spring arm 22 may be a separate spring component that is mounted to the pawl 18.

Figure 10A:
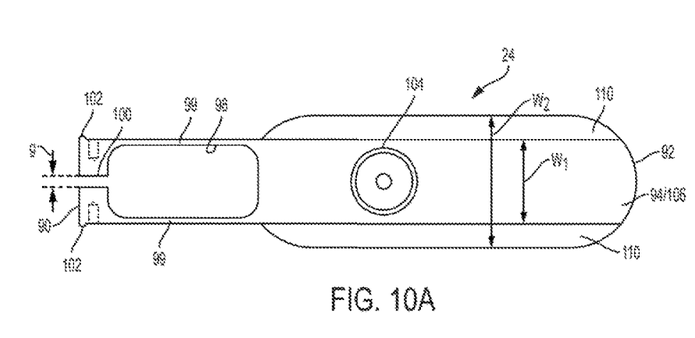
FIG. 10A is a top plan view of the carriage of the instrument of FIG. 1.
Figure 10B:
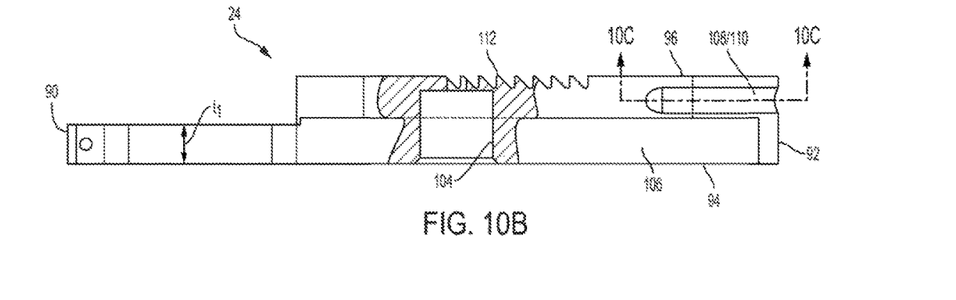
FIG. 10B is a side elevation view of the carriage of FIG. 10A, a portion of which is shown cut-away to reveal a hole for receiving a central roller.
Figure 10C:
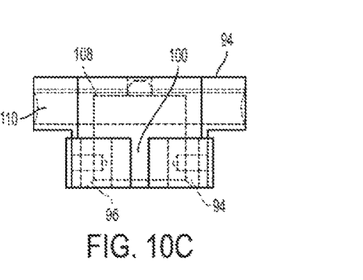
FIG. 10C depicts a front elevation view of the carriage of FIG. 10A.

FIGS. 10A-10C depict the carriage 24 of the instrument 10. The carriage 24 is an elongated body having a proximal end 90, a distal end 92, a top surface 94, and a bottom surface 96 opposite the top surface 94. The proximal end 90 has a reduced thickness $t_1$ as compared with the distal end 92.

A cutout 98 is formed at the reduced thickness proximal end 90. A channel 100 intersects the cutout 98 and extends through the proximal end 90, thereby resulting in two opposing flexible arms 99 that can flex with respect to each other. The channel 100 has a gap width 'g', which enables the flexible arms 99 to flex relative to one another.

A tooth 102, in the form of a rounded protrusion, is formed at the outwardly facing proximal end of each flexible arm 99. The teeth 102 are configured to engage with the opposing sets of teeth 62 (see FIG. 7D) of the handle 12 to limit (but not prevent) translation of the carriage 24 with respect to the handle 12, as will be described with reference to operation of the instrument 10. Alternatively, pins may protrude from the arms 99 (in the same direction as the teeth 102) for engaging the teeth 62.

The arms 99 may also be referred to herein as friction members. Those skilled in the art will recognize that other devices exist for introducing friction between two components that move relative to one another.

A hole 104 is formed on the top surface 94 at a location intermediate the proximal and distal ends 90 and 92. The hole 104 is configured to receive the central roller 28 in either a removable or non-removable fashion.

The top portion 106 of the carriage 24, which includes the top surface 94 and the flexible arms 99, has an overall width W1 which is less than an overall width W2 of the bottom portion 108 that includes the bottom surface 96. The bottom portion 108 includes two rails 110 which extend from opposing sides of the carriage 24. In an assembled form of the instrument 10, the rails 110 are positioned in the channel 60 of the handle 12 such that the carriage 24 can slide within the channel 60 and respect to the handle 12. The carriage 24 is prevented from moving in the vertical direction relative to the handle 12 by the shoulders 63 (FIG. 7C) of the handle 12.

A series of right-angle ratchet teeth 112 are defined on the bottom surface 96 of the carriage 24 for meshing with the tooth 86 of the pawl 18. The ratchet teeth 112 are angled so that, in the distal translational direction of the tooth 86, the tooth 86 bears on one tooth of the teeth 112 to translate the carriage 24; and in the proximal translational direction of the tooth 86, the tooth 86 slides past the teeth 112.

As best shown in FIGS. 1-5, in the assembled form of the instrument 10, the lever 14 is pivotably connected to the handle 12 about the pin 16. The pin 16 defines the axis of rotation of the lever 14. The longitudinal axis 132 of the pin 16 may be referred to herein as the pivot axis of the lever 14. The springs 38 and 42 are coupled together to bias the lever 14 away from the handle 12. The pawl 18 is pivotably connected to the lever 14 about the cylinder 88. The cylinder 88 defines the axis of rotation of the pawl 18. The tooth 86 of the pawl 18 meshes with the teeth 112 of the carriage 24.

The tooth 86 is biased against the teeth 112 by the spring arm 22 of the pawl 18. The spring arm 22 is positioned to bear on a surface at the distal end 72 of the lever 14. The other teeth 102 of the carriage 24 are meshed with the teeth 62 of the handle 12 to control translational movement of the carriage 24 with respect to the handle 12.

The central roller 28 is positioned between and proximal of the side rollers 30a and 30b. A gap 128a is formed between the central roller 28 and the side roller 30a, and an equally sized gap 128b is formed between the central roller 28 and the side roller 30b. The size of the gaps 128a and 128b and the relative position of the central roller 28 with respect to the side rollers 30a and 30b can be adjusted by moving the lever 14, as will be described with reference to operation of the instrument 10. A rod 130 (shown only in FIG. 1) is configured to be positioned within the gaps 128a and 128b, and bent by the instrument 10. The rod 130 is bent around the longitudinal axis 131 (see FIG. 4) of the central roller 28. The longitudinal axis 131 of the central roller 28 is referred to as the "bending axis."

The bending axis 131 is oriented orthogonal to the pivot axis 132 of the lever 14 and orthogonal to a longitudinal axis of the rod 130. Also, the pivot axis 132 is oriented parallel to the longitudinal axis of the elongated rod 130. In this manner, a user can squeeze (or otherwise manipulate) the lever 14 with a single hand while viewing the rod 130 bend about the bending axis 131 and without rotating his or her wrist.

A template rod 32 may be mounted to the clip 29, as shown in FIG. 3. The template rod 32 provides a template for bending the rod 130. In other words, a physician can use the template rod 32 as a template or guide while he or she bends the rod 130, and the rod 130 can be bent to the same (or different) degree as the template rod 32. The template rod 32 is removably positioned within the arms of the clip 29, and may be exchanged with a template rod having a different degree of bend.

The individual components of the instrument 10 may be fabricated from stainless steel, for example, or any other materials known to those skilled in the art.

Figure 5:
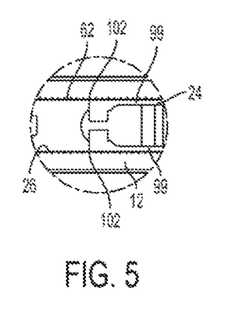
FIG. 5 is a detailed view of one area of FIG. 3.
Figure 6:
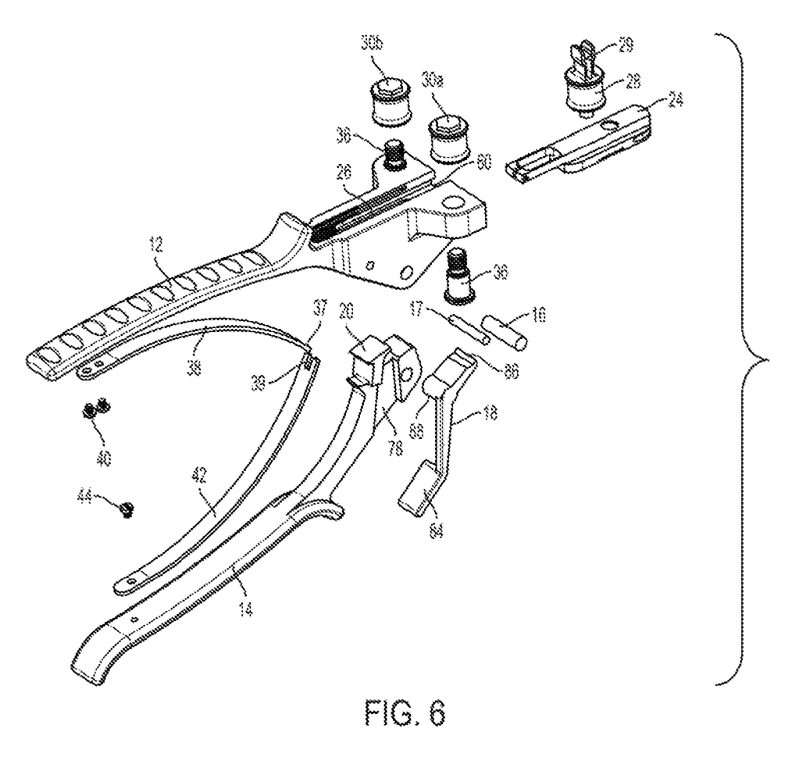
FIG. 6 is an exploded view of the instrument of FIG. 1.

Referring now to the process of operating the instrument 10 with reference to FIGS. 3-5, a physician first attaches a template rod 32 to the clip. This step is optional. The physician then places a rod 130, which may be either straight or bent, between the central roller 28 and the side rollers 30a and 30b. At this stage, there is sufficient clearance space within the gaps 128a and 128b to allow the physician to easily place the rod 130 between the central roller 28 and the side rollers 30a and 30b.

The physician then grasps the handle 12 and the lever 14 with one hand and squeezes the lever 14 toward the handle 12 against the biasing force of the springs 38 and 42. As the lever 14 rotates about the pin 16 (and the pivot axis 132) toward the handle 12, the pawl 18 rotates in the same direction along with the lever 14. As the pawl 18 rotates, the tooth 86 of the pawl 18 bears on a tooth of the ratchet teeth 112 of the carriage 24, thereby driving the carriage 24 in the distal direction (i.e., toward the side rollers 30a and 30b and the distal end 43 of the handle 12). As the carriage 24 is moved in the distal direction, the rod 130 becomes compressed between the rollers 28, 30a and 30b and bent about the bending axis 131. The solid interconnection between the lever 14, the pawl 18 and the carriage 24 provides a mechanical advantage as the lever 14 is pivoted about pivot axis 132.

The carriage 24 is driven in the distal direction by a force that exceeds the flexure strength of the arms 99. Accordingly, as the carriage 24 is moved in the distal direction, the teeth 102 at the proximal end of the flexible arms 99 of the carriage 24 ride over the teeth 62 of the handle 12. The flexible arms 99 flex inwardly and outwardly in a successive fashion as the teeth 102 of the flexible arms 99 ride over the teeth 62 of the handle 12. The carriage 24 is driven in the distal direction until either the physician releases the lever 14, or the lower wall 77*c* (FIG. 8C) of the slot 19 bears on the stationary pin 17.

As noted above, because the bending axis 131 is oriented orthogonal to the pivot axis 132 of the lever 14, the physician can squeeze (or otherwise manipulate) the lever 14 with a single hand while viewing the rod 130 bend about the bending axis 131 and without rotating his or her wrist.

As the physician releases the lever 14, the springs 38 and 42 pivots the lever 14 outwardly. Also, the tooth 86 of the pawl 18 slides backwards (in the proximal direction) along the surfaces of the teeth 112 of the carriage 24 without moving the carriage 24. The lever 14 pivots outwardly under the force of the springs 38 and 42 until the top wall 77*b* (FIG. 8C) of the slot 19 of the lever 14 contacts the stationary pin 17, as shown in FIG. 4.

The carriage 24 remains stationary as the tooth 86 of the pawl 18 slides in the proximal direction along the teeth 112 because of the engagement between the teeth 102 of the carriage 24 and the teeth 62 of the handle 12. In other words, the engagement between the teeth 102 of the carriage 24 and the teeth 62 of the handle 12 prevent the carriage 24 from returning to its initial positon (i.e., moving proximally) as the tooth 86 of the pawl 18 slides backwards along the surfaces of the teeth 112 of the carriage 24. Because the carriage 24 remains stationary through ratcheting action of the teeth 62, 86, 102, and 112, the rod 130 remains compressed between the rollers 28, 30*a* and 30*b*.

If further bending of the rod 130 is required, then the physician repeats the above-described squeezing and releasing steps, thereby driving the carriage 24 and the central roller 28 further in the distal direction and producing a larger bend in the rod 130.

If a template rod 32 is mounted to the clip 29, then the physician may use the template rod 32 as a guide for determining the appropriate bend of the rod 130.

Once no further bending of the rod 130 is required, the physician releases the lever 14 and then depresses the finger tab 84 of the pawl 18 toward the lever 14 against the force of the spring 22, which causes the pawl 18 to pivot about the cylinder 88 in a clockwise direction (as viewed in FIG. 4), which causes the tooth 86 of the pawl 18 to separate and disconnect from the teeth 112 of the carriage 24. The physician then manually translates the carriage 24 backwards in the proximal direction with a force that exceeds the flexure strength of the arms 99. When the physician translates the carriage 24 backwards, the flexible arms 99 of the carriage 24 will consequently flex inwardly and outwardly as the teeth 102 of the carriage 24 move backwards in the proximal direction and ride over the teeth 62 of the handle 12. The physician can then remove the bent rod 130 from the instrument 10.

The carriage 24 can be removed from the instrument 10 for cleaning or replacement, for example, by manually moving the carriage 24 forwards in the distal direction while the finger tab 84 remains depressed.

Although this description makes reference to specific embodiments and illustrations, the invention is not intended to be limited to the details shown. Rather, the invention encompasses various modifications and combinations of the specific embodiments and illustrations that may be made within the scope and range of equivalents of the claims.

For example, in another exemplary embodiment of the invention, the pawl is integrated with the lever and is, thus, incapable of pivoting with respect to the lever.

Accordingly, it is intended that the appended claims cover all such variations as fall within the scope of the invention.

What is claimed:

1. An instrument for bending a surgical implant about a bending axis, comprising:
   a handle defining a receiving area for receiving the surgical implant;
   a lever pivotably connected to the handle about a pivot axis that is orthogonal to the bending axis; and
   a movable linkage connected to the lever for movement therewith, the moveable linkage being configured to bend the surgical implant about the bending axis upon pivoting the lever about the pivot axis,
   the movable linkage comprising a carriage that is translatable on the handle upon pivoting the lever about the pivot axis,
   the carriage including a friction member that is configured to engage with a friction surface on the handle as the carriage is translated with respect to the handle, and
   the friction member comprising a flexible arm having a tooth, and the friction surface comprising a toothed surface defined on the handle.

2. The instrument of claim 1, wherein the movable linkage further comprises a pawl that is configured to engage the carriage for moving the carriage toward the surgical implant.

3. The instrument of claim 2, wherein the pawl is pivotably connected to the lever between a first position and a second position, wherein, in the first position of the pawl, the pawl is engaged with the carriage, and, in the second position of the pawl, the pawl is disengaged from the carriage.

4. The instrument of claim 2, wherein the carriage includes ratchet teeth and the pawl includes a ratchet tooth, wherein in one rotational direction of the lever, the ratchet tooth is configured to engage the ratchet teeth to cause the carriage to translate toward the surgical implant, and, in an opposite rotational direction of the lever, the ratchet tooth is configured to slide over the ratchet teeth resulting in no movement of the carriage.

5. The instrument of claim 4 further comprising a spring for biasing the ratchet tooth of the pawl against the ratchet teeth of the carriage.

6. The instrument of claim 1, wherein the carriage is slidably mounted in a channel disposed in the handle.

7. An instrument for bending a surgical implant about a bending axis, comprising:
   a handle defining a receiving area for receiving the surgical implant;
   a lever pivotably connected to the handle about a pivot axis that is orthogonal to the bending axis;
   a movable linkage connected to the lever for movement therewith, the moveable linkage being configured to bend the surgical implant about the bending axis upon pivoting the lever about the pivot axis;
   the movable linkage comprising a carriage that is translatable on the handle upon pivoting the lever about the pivot axis;
   a central roller mounted to the carriage;
   side rollers mounted to the handle adjacent the central roller;

a space formed between the central roller and the side rollers in which the surgical implant is configured to be positioned; and a template rod holder mounted to the central roller, wherein movement of the central roller toward the side rollers causes the surgical implant to bend about the bending axis.

8. An instrument for bending a surgical implant, comprising:

a handle defining a receiving area for receiving the surgical implant;

a lever pivotably connected to the handle about a pivot axis; and a movable linkage connected to the lever, the moveable linkage being configured to translate in a first direction to bend the surgical implant about a bending axis upon pivoting the lever about the pivot axis;

a friction member extending from the moveable linkage for limiting translation of the moveable linkage in a second direction that is opposite the first direction upon releasing the lever;

the movable linkage comprising a carriage that is translatable on the handle upon pivoting the lever about the pivot axis;

the carriage including the friction member that is configured to engage with a friction surface on the handle as the carriage is translated with respect to the handle; and the friction member comprising a flexible arm having a tooth, and the friction surface comprising a toothed surface defined on the handle.

9. The instrument of claim 8, wherein the friction member is also configured to limit translation of the moveable linkage in the first direction.

10. The instrument of claim 8, wherein the movable linkage further comprises a pawl that is configured to engage the carriage for moving the carriage toward the surgical implant.

11. The instrument of claim 10, wherein the pawl is pivotably connected to the lever between a first position and a second position, wherein, in the first position of the pawl, the pawl is engaged with the carriage, and, in the second position of the pawl, the pawl is disengaged from the carriage.

12. The instrument of claim 10, wherein the carriage includes ratchet teeth and the pawl includes a ratchet tooth, wherein in one rotational direction of the lever, the ratchet tooth is configured to engage the ratchet teeth to cause the carriage to translate toward the surgical implant, and, in an opposite rotational direction of the lever, the ratchet tooth is configured to slide over the ratchet teeth resulting in no movement of the carriage.

13. An instrument for bending a surgical rod, comprising:

a handle defining a receiving area for receiving the surgical rod;

a lever pivotably connected to the handle; and a template rod holder mounted to one of the handle and the lever at a location adjacent the receiving area, the template rod holder being configured for holding a template rod having a bent shape that can be used as a template for bending the surgical rod about a bending axis;

a movable linkage connected to the lever, the moveable linkage being configured to bend the surgical rod upon pivoting the lever;

the movable linkage comprising a carriage that is translatable on the handle upon pivoting the lever;

a central roller mounted to the carriage;

side rollers mounted to the handle adjacent the central roller; and a space formed between the central roller and the side rollers in which the surgical rod is configured to be positioned, wherein movement of the central roller toward the side rollers causes the surgical rod to bend about the bending axis, and wherein the template rod holder is mounted to the central roller.

* * * * *